US008852571B2

(12) United States Patent
Pittenger et al.

(10) Patent No.: US 8,852,571 B2
(45) Date of Patent: *Oct. 7, 2014

(54) CARDIAC MUSCLE REGENERATION USING MESENCHYMAL STEM CELLS

(75) Inventors: Mark F. Pittenger, Severna Park, MD (US); Stephen L. Gordon, Columbia, MD (US); Alastair Morgan Mackay, Timonium, MD (US); Bradley J. Martin, Ellicott City, MD (US)

(73) Assignee: Mesoblast International Sarl (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/369,917

(22) Filed: Feb. 9, 2012

(65) Prior Publication Data

US 2012/0141437 A1 Jun. 7, 2012

Related U.S. Application Data

(63) Continuation of application No. 13/012,956, filed on Jan. 25, 2011, now Pat. No. 8,158,121, which is a continuation of application No. 12/395,949, filed on Mar. 2, 2009, now Pat. No. 7,892,829, which is a continuation of application No. 10/690,435, filed on Oct. 21, 2003, now Pat. No. 7,514,074, which is a continuation-in-part of application No. 10/278,148, filed on Oct. 22, 2002, now abandoned, which is a continuation-in-part of application No. 10/127,737, filed on Apr. 22, 2002, now abandoned, which is a continuation of application No. 09/446,952, filed as application No. PCT/US98/14520 on Jul. 14, 1998, now Pat. No. 6,387,369.

(60) Provisional application No. 60/052,910, filed on Jul. 14, 1997.

(51) Int. Cl.
| A61K 48/00 | (2006.01) |
| C12N 15/85 | (2006.01) |
| C12N 5/077 | (2010.01) |
| C12N 5/0775 | (2010.01) |
| A61K 35/12 | (2006.01) |

(52) U.S. Cl.
CPC ......... *C12N 5/0657* (2013.01); *A61K 2035/124* (2013.01); *A61K 35/12* (2013.01); *C12N 2500/99* (2013.01); *C12N 2533/54* (2013.01); *C12N 5/0663* (2013.01); *A61K 48/00* (2013.01); *C12N 2510/02* (2013.01)
USPC ........................................ 424/93.1; 435/325

(58) Field of Classification Search
USPC .......................................... 424/93.1; 435/325
See application file for complete search history.

(56) References Cited

U.S. PATENT DOCUMENTS

| 5,226,914 A | 7/1993 | Caplan et al. |
| 5,486,359 A | 1/1996 | Caplan et al. |
| 5,591,625 A | 1/1997 | Gerson et al. |
| 5,716,616 A | 2/1998 | Prockop et al. |
| 5,846,796 A | 12/1998 | Cerami et al. |
| 6,099,832 A | 8/2000 | Mickle et al. |
| 6,387,369 B1 | 5/2002 | Pittenger et al. |
| 7,015,037 B1 | 3/2006 | Furcht et al. |
| 7,514,074 B2 | 4/2009 | Pittenger et al. |
| 8,075,881 B2 | 12/2011 | Verfaillie et al. |
| 8,486,696 B2 | 7/2013 | Ho et al. |
| 2007/0003530 A1 | 1/2007 | Pittenger et al. |

FOREIGN PATENT DOCUMENTS

| WO | 94/00484 | 1/1994 |
| WO | 96/30031 | 10/1996 |
| WO | 99/03973 | 1/1999 |
| WO | 00/06701 | 7/1999 |
| WO | 99/49015 | 9/1999 |
| WO | 0017326 | 3/2000 |
| WO | 2004/084921 | 10/2004 |

OTHER PUBLICATIONS

Pittenger et al (Circ Res, 95: 9-20, 2004).*
Barbash et al (Circulation, 108: 863-868, 2003).*
Office Action in U.S. Appl. No. 13/012,953, dated Jun. 28, 2011.
Office Action in U.S. Appl. No. 13/012,953, dated Aug. 10, 2011.
Office Action in U.S. Appl. No. 12/725,867, dated Jul. 25, 2011.
Martin et al., Blood, 66:664-672 (1995).
Torre-Amione et al., JACC, 27:1201-1206 (1996).
Nagaya et al., Circulation, 1122:1128-1135 (2005).
Yanagisawa-Miwa et al., Science, 257:1401-1403 (1992).
Auerbach et al., Biology of Endothelial Cells, ed. Jaffe, E. (Nijhoff, Boston) pp. 393-400 (1984).
Risau, PNAS USA, 83:3855-3859 (1986).
Office Action in U.S. Appl. No. 12/725,867, dated May 5, 2011.
Wagers et al., Cell, 116:639-648 (2004).
Wakitani et al., Myogenic Cells Derived from Rat Bone Marrow Mesenchymal Stem Cells Exposed to 5-Azacytidine, Muscle & Nerve, 18(12):1417-1426 (1995).
Warejcka et al., A Population of Cells Isolated from Rat Heart Capable of Differentiating into Several Mesodermal Phenotypes, J. Surg. Res., 62:233-242 (1996).
Written Opinion in PCT/US98/14520, dated Jun. 23, 1999.
Fukuda, "Development of regenerative cardiomyocytes from mesenchymal stem cells for cardiovascular tissue engineering," Artif. Organs, 25(3):187-193 (2001).

(Continued)

*Primary Examiner* — Marcia S Noble
*Assistant Examiner* — Magdalene Sgagias
(74) *Attorney, Agent, or Firm* — McAndrews, Held & Malloy, Ltd.

(57) ABSTRACT

Disclosed is a method for producing cardiomyocytes in vivo by administering to the heart of an individual a cardiomyocyte producing amount of mesenchymal stem cells. These cells can be administered as a liquid injectible or as a preparation of cells in a matrix which is or becomes solid or semisolid. The cells can be genetically modified to enhance myocardial differentiation and integration. Also disclosed is a method for replacing cells ex vivo in a heart valve for implantation.

10 Claims, 7 Drawing Sheets

(56) References Cited

OTHER PUBLICATIONS

Hughes, "Cardiac stem cells," J. Pathol., 197(4):468-478 (2002).
International Search Report in PCT/US03/33450, dated Jan. 28, 2005.
Liechty et al., "Human mesenchymal stem cells engraft and demonstrate site-specific differentiation after in utero transplantation in sheep," Nat. Med., 6(11):1282-1286 (2000).
Min et al., "Effects of co-transplantation of cultured human mesenchymal stem cells plus fetal cardiomyocytes on cardiac function in infarcted pigs," Circulation, 104:11-289 (2001).
Min et al., "Significant improvement of heart function by cotransplantation of human mesenchymal stem cells and fetal cardiomyocytes in postinfarcted pigs," Ann. Thorac. Surg., 74(5):1568-1575 (2002).
Office Action in U.S. Appl. No. 12/725,867, dated Dec. 22, 2011.
Saito et al., "Xenotransplant cardiac chimera: immune tolerance of adult stem cells," Ann. Thorac. Surg., 74:19-24 (2002).
Toma et al., "Human mesenchymal stem cells differentiate to a cardiomyocyte phenotype in the adult murine heart," Circulation, 105(1):93-98 (2002).
Wang et al., "The coronary delivery of marrow stromal cells for myocardial regeneration: Pathophysiologic and therapeutic implications," J. Thorac. Cardiovasc. Surg., 122(4):699-705 (2001).
Office Action in U.S. Appl. No. 13/012,956, dated Jul. 21, 2011.
Office Action in U.S. Appl. No. 13/012,956, dated Sep. 1, 2011.
Breitbach et al., Blood, 110:1362-1369 (2007).
Bruder et al., Mesenchymal Stem Cells in Bone Development, Bone Repair, and Skeletal Regeneration Therapy, J. Cell. Biochem., 56:283-294 (1994).
Chen et al., Stroke, 32:1005-1011 (2001).
Chen, J. Neurol. Sci., 189:49-57 (2001).
Chiu et al., Ann. Therac. Surg., 60:12-18 (1995).
Chopp et al., The LANCET Neurology, 1:92-100 (2002).
Dalton et al., J. Cell. Biochem., Supp. 17E, Abstract R 202 (1993).
Deisher et al., U.S. Appl. No. 60/079,132 , 1998.
European Search Report corresponding to European Patent Application Serial No. 03776501.3-1222, dated Oct. 19, 2009.
Galinanes et al., Cell Transplantation, 13:7-13 (2004) (Abstract).
Gerson, Nature Med., 5:262-264 (1999).
Grigoriadis et al., Differentiation of Muscle, Fat, Cartilage, and Bone from Progenitor Cells Present in a Bone-derived Clonal Cell Population: Effect of Dexamethasone, J. Cell Biol., 106:2139-2151 (1988).
International Preliminary Examination Report in PCT/US98/14520, dated Sep. 3, 1999.
International Search Report in PCT/US98/14520, dated Oct. 13, 1998.
Jorgensen et al., Curr. Opin. Biotechnol., 15:406-410 (2004).
Kassem, Cloning and Stem Cells, 6(4):369-375 (2004).
Klug et al., Genetically Selected Cardiomyocytes from Differentiating Embroyonic Stem Cells from Stable Intracardiac Grafts, J. Clin. Invest., 98(1):216-224 (1996).
Krebsbach et al., Bone Formation In Vivo: Comparison of Osteogenesis by Transplanted Mouse and Human Marrow Stromal Fibroblasts, Transplantation, 63:1059-1069 (1997).
Lee et al., Ann. Intern. Med., 140:729-737 (2004).
Li et al., Neurology, 59:514-523 (2002).
Lin et al., Natural Killer Cell- and Macrophage-Mediated Rejection of Concordant Xenografts in the Absence of T and B Cell Responses, J. Immunol., pp. 5658-5667 (1997).
Martin et al., "Allogeneic mesenchymal stem cell engraftment in the infracted rat heart: Timing and delivery route." Bone Marrow Transplantation, vol. 29, No. S2, Mar. 2002, XP002549207.
Minguell et al., Exp. Biol. Med., 226:507-520 (2001).
Office Action in U.S. Appl. No. 09/446,952, dated Jan. 18, 2001.
Office Action in U.S. Appl. No. 09/446,952, dated Jun. 6, 2000.
Office Action in U.S. Appl. No. 10/690,435, dated Aug. 18, 2008.
Office Action in U.S. Appl. No. 10/690,435, dated Jan. 12, 2006.
Office Action in U.S. Appl. No. 10/690,435, dated Jan. 29, 2008.
Office Action in U.S. Appl. No. 10/690,435, dated Jul. 17, 2007.
Office Action in U.S. Appl. No. 10/690,435, dated Mar. 22, 2007.
Office Action in U.S. Appl. No. 10/690,435, dated Nov. 3, 2005.
Office Action in U.S. Appl. No. 10/690,435, dated Sep. 22, 2006.
Office Action in U.S. Appl. No. 11/475,568, dated Apr. 3, 2008.
Office Action in U.S. Appl. No. 11/475,568, dated Dec. 12, 2007.
Office Action in U.S. Appl. No. 12/395,949, dated Jan. 12, 2010.
Office Action in U.S. Appl. No. 12/395,949, dated Jun. 22, 2010.
Orkin et al., in Report and Recommendations of the Panel to Assess the NIH Investment in Research on Gene Therapy (1995).
Ott et al., Basic Res. Cardiol., 100:504-517 (2005).
Parmley et al., West J. Med., 154:427-441 (1991).
Pereira et al., Cultured adherent cells from marrow can serve as long-lasting precursor cells for bone, cartilage, and lung in irradiated mice, Proc. Natl. Acad. Sci. USA< 92:4857-4861 (1995).
Pfeffer et al., Circulation, 81:1161-1172 (1990).
Prockop, Science, 276:71-74 (1997).
Ramachandran et al., Plasma Homocysteine and Risk for Congestive Heart Failure in Adults Without Prior Myocardial Infarction, JAMA, 289(10):1251-1257 (2003).
Robinson et al., "Implantation of Skeletal Myoblast—Derived Cells," in Cellular Cardiomyoplasty: Myocardial Repair with Cell Implantation, Kao et al., eds., Landes Bioscience, pp. 81-107 (1997).
Saadi et al., Life Sciences, 62:365-387 (1998).
Saito et al., Tissue Engineering, 1(4):327-343 (1995).
Semedo et al., Transplantation Proceedings, 39:421-423 (2007).
Shake et al., The Annals of Thoracic Surgery, 73:1919-1926 (2002).
Szabolcs et al., Apoptosis of Cardiac Myocytes During Cardiac Allograft Rejection, Circulation, 94(7):1665-1673 (1996).
Verma et al., Nature, 389:239-242 (1997).
Roobrouck et al. Stem Cells; 29:871-882 (2011) (p. 874, first paragraph).
Nagaya et al. Am J Physiol Heart Circ Physiol; 287:H2670-H2676 (2004).
Freyman et al. European Heart Journal; 27:1114-1122 (2006).
Dai et al. Circulation; 112:214-223 (2005).
Kim et al. Circulation; 112[suppl I]:I-96I-104 (2005).
Amado et al. PNAS; 102(32):11474-11479 (2005).
Van't Hof et al. Cytotherapy; 9(5):477-487 (2007).
Van't Hof et al. In: Stem Cells and Myocardial Regeneration; Chap. 4:45-56, 2007.
Zeng et al. Circulation 115:1866-1875 (2007).

* cited by examiner

CONTROL
8 WKS POST MI
(PIG 20)

INJURED ANT.
LV WALL

ALTO MSC
8 WKS POST MI/MSC
(PIG 18)

INJURED ANT.
LV WALL

H&E (20x)

DAPI LABELED MSCs

FACTOR 8 RELATED PROTEIN
(VON WILLEBRAND FACTOR)

H&E

DAPI & VEG-F

CARDIAC MUSCLE REGENERATION USING MESENCHYMAL STEM CELLS

RELATED APPLICATIONS

This application is a continuation of application Ser. No. 13/012,956, filed on Jan. 25, 2011, which is a continuation of application Ser. No. 12/395,949, filed on Mar. 2, 2009 (now U.S. Pat. No. 7,892,829 issued on Feb. 22, 2011), which is a continuation of application Ser. No. 10/690,435, filed Oct. 21, 2003 (now U.S. Pat. No. 7,514,074 issued on Apr. 7, 2009), which is a continuation-in-part of application Ser. No. 10/278,148, filed Oct. 22, 2002 (now abandoned), which is a continuation-in-part of application Ser. No. 10/127,737, filed Apr. 22, 2002 (now abandoned), which is a continuation of application Ser. No. 09/446,952 (now U.S. Pat. No. 6,387,369 issued on May 14, 2002), which is the national phase application of PCT Application No. PCT/US98/14520, filed Jul. 14, 1998, which claims priority of U.S. provisional application Ser. No. 60/052,910, filed Jul. 14, 1997, the contents of which are incorporated by reference in their entirety.

FEDERALLY SPONSORED RESEARCH OR DEVELOPMENT

[Not Applicable]

BACKGROUND OF THE INVENTION

This invention relates to the replacement and regeneration of cardiac tissue and muscle.

This year over 300,000 Americans will die from congestive heart failure. The ability to augment weakened cardiac muscle would be a major advance in the treatment of cardiomyopathy and heart failure. Despite advances in the medical therapy of heart failure, the mortality due to this disorder remains high, where most patients die within one to five years after diagnosis.

A common heart ailment in the aging population is improper heart valve function, particularly the aortic valve. Mechanical replacement valves are widely used but require the patient to continually take blood thinners. Valves obtained from cadavers and xenographs (porcine) are also frequently used to replace a patient's own tissue. Valves are freeze-dried or chemically cross-linked using e.g., glutaraldehyde to stabilize the collagen fibrils and decrease antigenicity and proteolytic degradation. However, these valves remain acellular and often fail after several years due to mechanical strain or calcification. A replacement valve derived from biocompatible material that would allow ingrowth of the appropriate host cells and renewal of tissue over time would be preferred.

Mesenchymal stem cells (MSCs) are cells which are capable of differentiating into more than one type of mesenchymal cell lineage. Mesenchymal stem cells (MSCs) have been identified and cultured from avian and mammalian species including mouse, rat, rabbit, dog and human (See Caplan, 1991, Caplan et al. 1993 and U.S. Pat. No. 5,486,359). Isolation, purification and culture expansion of hMSCs is described in detail therein.

SUMMARY OF THE INVENTION

In accordance with the present invention mesenchymal stem cells (MSCs) are used to regenerate or repair striated cardiac muscle that has been damaged through disease or degeneration. The MSCs differentiate into cardiac muscle cells and integrate with the healthy tissue of the recipient to replace the function of the dead or damaged cells, thereby regenerating the cardiac muscle as a whole. Cardiac muscle does not normally have reparative potential. The MSCs are used, for example, in cardiac muscle regeneration for a number of principal indications: (i) ischemic heart implantations, (ii) therapy for congestive heart failure patients, (iii) prevention of further disease for patients undergoing coronary artery bypass graft, (iv) conductive tissue regeneration, (v) vessel smooth muscle regeneration and (vi) valve regeneration. Thus the MSCs are also used to integrate with tissue of a replacement heart valve to be placed into a recipient. The MSCs, preferably autologous, repopulate the valve tissue, enabling proper valve function.

MSC cardiac muscle therapy is based, for example, on the following sequence: harvest of MSC-containing tissue, isolation/expansion of MSCs, implantation into the damaged heart (with or without a stabilizing matrix and biochemical manipulation), and in situ formation of myocardium. This approach is different from traditional tissue engineering, in which the tissues are grown ex vivo and implanted in their final differentiated form. Biological, bioelectrical and/or biomechanical triggers from the host environment may be sufficient, or under certain circumstances, may be augmented as part of the therapeutic regimen to establish a fully integrated and functional tissue.

Accordingly, one aspect of the present invention provides a method for producing cardiomyocytes in an individual in need thereof which comprises administering to said individual a myocardium-producing amount of mesenchymal stem cells. The mesenchymal stem cells that are employed may be a homogeneous composition or may be a mixed cell population enriched in MSCs. Homogeneous human mesenchymal stem cell compositions are obtained by culturing adherent marrow or periosteal cells; the mesenchymal stem cells may be identified by specific cell surface markers which are identified with unique monoclonal antibodies. A method for obtaining a cell population enriched in mesenchymal stem cells is described, for example, in U.S. Pat. No. 5,486,359.

Cell preparations having greater than about 95%, usually greater than about 98%, of adult human bone marrow-derived stem cells can be achieved using techniques for isolation, purification, and culture expansion of stem cells. For example, isolated, cultured mesenchymal stem cells can comprise a single phenotypic population (about 95% or about 98% homogeneous) by flow cytometric analysis of expressed surface antigens. The desired cells in such composition can be identified, for example, by expression of a cell surface marker (e.g., CD73 or CD105) specifically bound by an antibody produced from hybridoma cell line SH2, ATCC accession number HB 10743, an antibody produced from hybridoma cell line SH3, ATCC accession number HB 10744, or an antibody produced from hybridoma cell line SH4, ATCC accession number HB 10745. Such antibodies selectively bind bone marrow-derived mesenchymal stem cells and, therefore, can be used to identify, quantify, isolate, or purify mesenchymal stem cells from bone marrow samples.

The administration of the cells can be directed to the heart, by a variety of procedures. Localized administration is preferred. The mesenchymal stem cells can be from a spectrum of sources including, in order of preference: autologous, allogeneic, or xenogeneic. There are several embodiments to this aspect, including the following.

In one embodiment of this aspect, the MSCs are administered as a cell suspension in a pharmaceutically acceptable liquid medium for injection. Injection, in this embodiment, can be local, i.e. directly into the damaged portion of the myocardium, or systemic. Here, again, localized administration is preferred.

In another embodiment of this aspect, the MSCs are administered in a biocompatible medium which is, or becomes in situ at the site of myocardial damage, a semi-solid or solid matrix. For example, the matrix may be (i) an injectible liquid which "sets up" (or polymerizes) to a semi-solid gel at the site of the damaged myocardium, such as collagen and its derivatives, polylactic acid or polyglycolic acid, or (ii) one or more layers of a flexible, solid matrix that is implanted in its final form, such as impregnated fibrous matrices. The matrix can be, for example, Gelfoam (Upjohn, Kalamazoo, Mich.). The matrix holds the MSCs in place at the site of injury, i.e. serves the function of "scaffolding". This, in turn, enhances the opportunity for the administered MSCs to proliferate, differentiate and eventually become fully developed cardiomyocytes. As a result of their localization in the myocardial environment they then integrate with the recipient's surrounding myocardium. These events likewise occur in the above liquid injectible embodiment, but this embodiment may be preferred where more rigorous therapy is indicated.

In another embodiment of this aspect, the MSCs are genetically modified or engineered to contain genes which express proteins of importance for the differentiation and/or maintenance of striated muscle cells. Examples include growth factors (TGF-β, IGF-1, FGF), myogenic factors (myoD, myogenin, Myf5, MRF), transcription factors (GATA-4), cytokines (cardiotrophin-1), members of the neuregulin family (neuregulin 1, 2 and 3) and homeobox genes (Csx, tinman, NKx family). Also contemplated are genes that code for factors that stimulate angiogenesis and revascularization (e.g. vascular endothelial growth factor (VEGF)). Any of the known methods for introducing DNA are suitable, however electroporation, retroviral vectors and adeno-associated virus (AAV) vectors are currently preferred.

Thus, in association with the embodiment of the above aspect using genetically engineered MSCs, this invention also provides novel genetically engineered mesenchymal stem cells and tissue compositions to treat the above indications. The compositions can include genetically modified MSCs and unmodified MSCs in various proportions to regulate the amount of expressed exogenous material in relationship to the total number of MSCs to be affected.

The invention also relates to the potential of MSCs to differentiate partially to the cardiomyocyte phenotype using in vitro methods. This technique can under certain circumstances optimize conversion of MSCs to the cardiac lineage by predisposing them thereto. This also has the potential to shorten the time required for complete differentiation once the cells have been administered.

BRIEF DESCRIPTION OF THE DRAWINGS

FIG. 1A shows the low magnification image of a rat heart which has been injected with dye labeled cells and later, a T-incision has been made at the site. FIGS. 1A and 1B reveal the labeled MSCs in the ventricle wall viewed from the outer surface. FIG. 1C shows a cross-section of the ventricle wall and that the cells are present in the outer 1-2 mm of the 3 mm thick cardiac muscle.

FIG. 6A is a hematoxylin and eosin stained section, while FIG. 6B is a fluorescent image showing the mesenchymal stem cells (dark, or blue) and of smooth muscle actin (light, or green), wherein the section was contacted with an FITC-labeled monoclonal antibody against smooth muscle actin.

FIGS. 7A and 7D are hematoxylin and eosin stained sections. FIG. 7B is a fluorescent image of DAPI-labeled mesenchymal stem cells. FIG. 7C is a fluorescent image showing the presence of DAPI-labeled mesenchymal stem cells (dark, or blue) and of Factor VIII (light, or green), wherein the section was contacted with an FITC labeled monoclonal antibody against Factor VIII. FIG. 7E is a fluorescent image showing the presence of DAPI-labeled mesenchymal stem cells (dark, or blue), and of vascular endothelial growth factor (VEGF), wherein the section was contacted with an FITC-labeled monoclonal antibody against VEGF.

DETAILED DESCRIPTION OF PREFERRED EMBODIMENTS

Figure 1A:
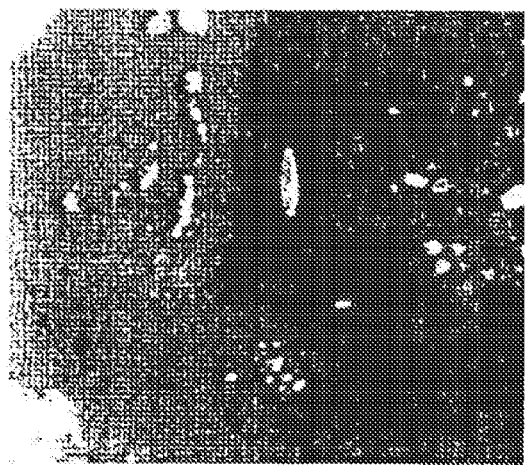
FIGS. 1A-1C show cardiac muscle injected, using a fine needle, with in vitro dye-labeled MSCs. The lipophilic dyes PKH26 (Sigma Chemical) or CM-Di I (Molecular Probes) were utilized to label MSCs prior to being introduced into animals. These dyes remain visible when the tissue site is harvested 1-2 months later. We have also shown that such dyes do not interfere with the differentiation of MSCs in in vitro assays.

The proper environmental stimuli convert MSCs into cardiac myocytes. Differentiation of mesenchymal stem cells to the cardiac lineage is controlled by factors present in the cardiac environment. Exposure of MSCs to a simulated cardiac environment directs these cells to cardiac differentiation as detected by expression of specific cardiac muscle lineage markers. Local chemical, electrical and mechanical environmental influences alter pluripotent MSCs and convert the cells grafted into the heart into the cardiac lineage.

Early in embryonic development following the epithelia-mesenchyme transition, the presumptive heart mesenchyme from the left and right sides of the body migrate to the ventral midline. Here, interaction with other cell types induces continued cardiogenesis. In vitro conversion of MSCs to cardiomyocytes is tested by co-culture or fusion with murine embryonic stem cells or cardiomyocytes, treatment of MSCs with cardiac cell lysates, incubation with specific soluble growth factors, or exposure of MSCs to mechanical stimuli and electrical stimulation.

A series of specific treatments applicable to MSCs to induce expression of cardiac specific genes are disclosed herein. The conditions are effective on rat, canine and human MSCs. Treatments of MSCs include (1) co-culturing MSCs with fetal, neonatal and adult rat cardiac cells, (2) use of chemical fusigens (e.g., polyethylene glycol or sendai virus) to create heterokaryons of MSCs with fetal, neonatal and adult cardiomyocytes, (3) incubating MSCs with extracts of mammalian hearts, including the extracellular matrix and related molecules found in heart tissue, (4) treatment of MSCs with growth factors and differentiating agents, (5) mechanical and/or electrical stimulation of MSCs, and (6) mechanically and/or electrically coupling MSCs with cardiomyocytes. MSCs that progress towards cardiomyocytes first express proteins found in fetal cardiac tissue and then proceed to adult forms. Detection of expression of cardiomyocyte specific proteins is achieved using antibodies to, for example, myosin heavy chain monoclonal antibody MF 20 (MF20), sarcoplasmic reticulum calcium ATPase (SERCA1) (mAb 10D1) or gap junctions using antibodies to connexin 43.

Cardiac injury promotes tissue responses which enhance myogenesis using implanted MSCs. Thus, MSCs are introduced to the infarct zone to reduce the degree of scar formation and to augment ventricular function. New muscle is thereby created within an infarcted myocardial segment. MSCs are directly infiltrated into the zone of infarcted tissue. The integration and subsequent differentiation of these cells is characterized, as described above. Timing of intervention is designed to mimic the clinical setting where patients with acute myocardial infarction would first come to medical attention, receive first-line therapy, followed by stabilization, and then intervention with myocardial replacement therapy if necessary.

Of the four chambers of the heart, the left ventricle is primarily responsible for pumping blood under pressure through the body's circulatory system. It has the thickest myocardial walls and is the most frequent site of myocardial injury resulting from congestive heart failure. The degree of advance or severity of the congestive heart failure ranges from those cases where heart transplantation is indicated as soon as a suitable donor organ becomes available to those where little or no permanent injury is observed and treatment is primarily prophylactic.

The severity of resulting myocardial infarction, i.e. the percentage of muscle mass of the left ventricle that is involved can range from about 5 to about 40 percent. This represents affected tissue areas, whether as one contiguous ischemia or the sum of smaller ischemic lesions, having horizontal affected areas from about 2 $cm^2$ to about 6 $cm^2$ and a thickness of from 1-2 mm to 1-1.5 cm. The severity of the infarction is significantly affected by which vessel(s) is involved and how much time has passed before treatment intervention is begun.

The mesenchymal stem cells used in accordance with the invention are, in order of preference, autologous, allogeneic or xenogeneic, and the choice can largely depend on the urgency of the need for treatment. A patient presenting an imminently life threatening condition may be maintained on a heart/lung machine while sufficient numbers of autologous MSCs are cultured or initial treatment can be provided using other than autologous MSCs.

The MSC therapy of the invention can be provided by several routes of administration, including the following. First, intracardiac muscle injection, which avoids the need for an open surgical procedure, can be used where the MSCs are in an injectible liquid suspension preparation or where they are in a biocompatible medium which is injectible in liquid form and becomes semi-solid at the site of damaged myocardium. A conventional intracardiac syringe or a controllable arthroscopic delivery device can be used so long as the needle lumen or bore is of sufficient diameter (e.g. 30 gauge or larger) that shear forces will not damage the MSCs. The injectible liquid suspension MSC preparations can also be administered intravenously, either by continuous drip or as a bolus. During open surgical procedures, involving direct physical access to the heart, all of the described forms of MSC delivery preparations are available options.

As a representative example of a dose range is a volume of at least about 20 µl, preferably at least 500 µl, of injectible suspension containing 10-40×$10^6$ MSCs/ml. The concentration of cells per unit volume, whether the carrier medium is liquid or solid remains within substantially the same range. The amount of MSCs delivered will usually be greater when a solid, "patch" type application is made during an open procedure, but follow-up therapy by injection will be as described above. The frequency and duration of therapy will, however, vary depending on the degree (percentage) of tissue involvement, as already described (e.g. 5-40% left ventricular mass).

In cases having in the 5-10% range of tissue involvement, it is possible to treat with as little as a single administration of one million MSCs in 20-50 µl of injection preparation. The injection medium can be any pharmaceutically acceptable isotonic liquid. Examples include phosphate buffered saline (PBS), culture media such as DMEM (preferably serum-free), physiological saline or 5% dextrose in water (D5W).

In cases having more in a range around the 20% tissue involvement severity level, multiple injections of 20-50 µl (10-40×$10^6$ MSCs/ml) are envisioned. Follow-up therapy may involve additional dosings.

In very severe cases, e.g. in a range around the 40% tissue involvement severity level, multiple equivalent doses for a more extended duration with long term (up to several months) maintenance dose aftercare may well be indicated.

When given intravenously, the mesenchymal stem cells may be administered in at least 20 µl, preferably at least 500 µl, and up to about 150 ml of a suspension containing 10-40×$10^6$ MSCs/ml. In one embodiment, from 40 ml to about 150 ml of a suspension containing 10-40×$10^6$ MSCs/ml is given intravenously.

Applicants also have discovered that the mesenchymal stem cells may stimulate and/or promote angiogenesis in the heart and/or repair or regenerate blood vessels of the heart. Thus, in accordance with another aspect of the present invention, there is provided a method of stimulating or promoting angiogenesis in the heart, or of repairing or regenerating blood vessels of the heart of an individual by administering to the individual mesenchymal stem cells in an amount effective to stimulate or promote angiogenesis, or repair or regenerate blood vessels of the heart. The mesenchymal stem cells may be administered as a cell suspension in a pharmaceutically acceptable liquid medium such as hereinabove described, or in a biocompatible medium which is, or becomes in situ at the site of myocardial damage, a semi-solid or solid matrix, also as hereinabove described.

The mesenchymal stem cells may be allogeneic, autologous, or xenogeneic, and may be administered in dosages such as those hereinabove described.

When the mesenchymal stem cells are administered as a cell suspension in a pharmaceutically acceptable liquid medium for injection, they may be administered locally, i.e., directly into the damaged portion of the heart, such as by an endocardial catheter for example, or they may be administered systemically, such as by intravenous administration.

The mesenchymal stem cells provide for the repair or regeneration of existing blood vessels of the heart, as well as promote angiogenesis, i.e., the formation of new blood vessels of the heart. Blood vessels which may be repaired or regenerated, as well as new blood vessels which may be formed, include arteries (including arterioles), and veins, as well as capillaries.

The present invention is further illustrated, but not limited, by the following examples.

EXAMPLE 1

Implantation of MSCs in Normal Cardiac Muscle

In using MSCs, it is desirable to maintain cell-cell contact in vivo for the conversion of MSCs to the muscle lineage. Environmental signals identified above act in concert with mechanical and electrical signaling in vivo to lead to cardiac differentiation.

Primary human MSCs (hMSCs) are introduced into athymic rat myocardial tissue by direct injection. The integration of implanted cells, their subsequent differentiation, formation of junctions with cardiac cells, and their long-term survival are characterized with light microscopy, histology, confocal immunofluorescence microscopy, electron microscopy and in situ hybridization.

Whether human MSCs are appropriately grafted into cardiac muscle of athymic rats (strain HSD:RH-RNU/RNU), which lack the immune responses necessary to destroy many foreign cells, is also examined.

Rat MSCs are grafted into the heart muscles of rats. To analyze the injected cells over several weeks and to minimize the possibility of immune system rejection, MSCs are harvested from Fisher 344 rats, the same inbred strain (identical genotype) as the intended MSC recipients.

The MSCs can be marked in a variety of ways prior to their introduction into the recipient. This makes it possible to trace the fate of the MSCs as they proliferate and differentiate in the weeks following the MSC implant. Several methods are utilized to identify positively the injected cells: membrane lipid dyes PKH26 or CM-DI I and genetic marking with adeno-associated virus (AAV) or retroviruses, such as Moloney murine leukemia virus expressing green fluorescent protein (GFP) or galactosidase. PCR also is used to detect the Y chromosome marker of male cells implanted into female animals. The dye-labeled cells are detected readily and offer the simplest method to directly follow the injected cells. This method is reliable for times out to at least 4 weeks. On the day of introduction to recipient animals, MSCs are trypsinized and labeled with CM-DI I according to the recommendations of the manufacturer (Molecular Probes). Subconfluent monolayer cultures of MSCs are incubated with 5 mM CM-DI I in serum-free medium for 20 minutes, trypsinized, washed twice in excess dye-free medium, and utilized for injection.

Alternatively, MSCs are genetically marked prior to injections, such as by using AAV-GFP vector. This vector lacks a selectable marker but mediates high-level expression of the transduced genes in a variety of post-mitotic and stem cell types. Recombinant AAV-GFP is added to low density monolayers of MSCs in low serum. Following a four hour incubation at 37° C., the supernatant is removed and replaced with fresh media. At 96 hours after transduction, cells are assayed for green fluorescent protein (GFP) activity. Typically 50% of the cells express the transduced gene. Unselected MSCs on a clonal line, isolated by limiting dilution, are utilized for injection. Cells are collected following trypsin treatment, washed and used at high concentrations for injection (10 to 100 million cells per ml).

Figure 1B:
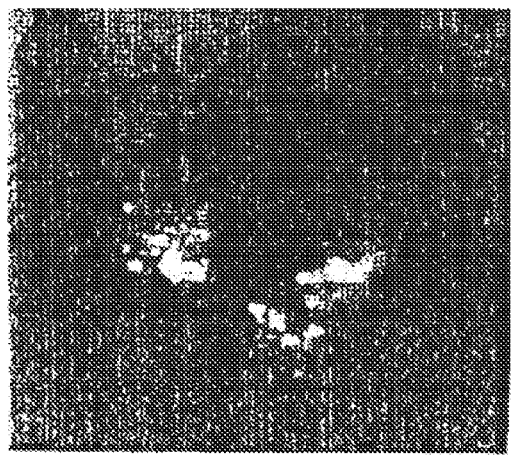
Figure 1C:
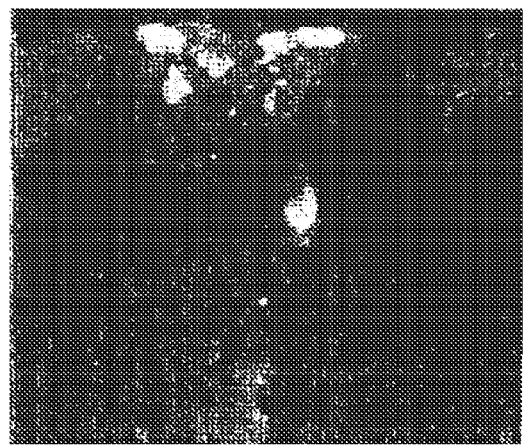

To test whether the hMSCs became cardiomyocytes in the heart environment, the hearts of ten week old athymic rats were injected with dye labeled or GFP-labeled human MSCs. All procedures were performed under strict sterile conditions. The animals were placed in a glass jar containing a methoxyflurane anesthesia soaked sponge. Under sterile conditions, a 20 mm anterior thoracotomy was performed, and following visualization of the left ventricle, 10 μl of the cell suspension, containing 10,000 to 100,000 MSCs in serum-free medium were injected into the left ventricular apex using a 30 gauge needle. The procedure was performed rapidly with endotracheal intubation and mechanical ventilation assist. The incision was closed with sutures. Ventilation assist was normally unnecessary after a short period following chest closure. FIG. 1A shows the low magnification image of a rat heart which was injected with dye labeled cells and later, a T-incision had been made at the site to reveal the injected cells in the ventricle wall. FIG. 1A is a gross photo of the incised heart. FIGS. 1B and 1C reveal the labeled MSCs in the ventricle wall. FIG. 1C shows that the cells were present in the outer 1-2 mm of the 3 mm thick rat cardiac muscle.

When sacrificed, the heart is removed, examined by light microscopy for the presence of vascular thrombi or emboli, paraffin-embedded, and sectioned. The histology of serial sections is examined to determine the fate of dye-stained cells. Sections then are tested for immunohistochemical markers of cardiac muscle in the areas of the introduced MSCs to ascertain whether donor MSCs have differentiated into cardiomyocytes in vivo. Implantation surgeries are carried out on animals to be sacrificed at 1, 2, 4, and 6 weeks (4 animals at each time point) and the hearts which received implants are analyzed histologically and immunologically.

For phenotypic characterization, the hearts are removed and processed for histology by immunofluorescence microscopy. Differentiation of MSCs is determined by the immunofluorescence localization of sacomeric myosin heavy chain, SERCA1 and phospholamban. The sequence-specific antibody to gap junction protein connexin 43, which is commercially available (Zymed) and detects gap junctions in cardiac tissue is used.

MSCs are also implanted in biomatrix materials to determine if enhanced grafting would be observed, such as Type I collagen. The MSCs are mixed rapidly with the matrix in a small volume and injected into the ventricle wall. The biomatrices are used at concentrations of 0.1 mg/ml or greater. For example, the biomatrices may be used at concentrations of 1 to 3 mg/ml containing 10 to 100 million cells/ml. The tissue is analyzed at times of 1, 2, 4, and 6 weeks as described above.

EXAMPLE 2

Regeneration of Heart Valves using MSCs

Xenograft or homograft valves are made acellular by freeze-drying, which leads to cellular death, or by enzymatic treatment followed by detergent extraction of cells and cell debris. This latter approach was taken by Vesely and coworkers with porcine valves to be repopulated with dermal or aortic fibroblasts. Curtil, et al. 1997 used a freeze-dried porcine valve and attempted repopulation of the valve with human fibroblasts and endothelial cells. These studies were preliminary and limited to short term studies in vitro.

The acellular valve to be populated by autologous hMSCs is incubated with culture expanded hMSCs in a tumbling vessel to ensure loading of cells to all valve surfaces. The valve is then cultured with the hMSCs for 1-2 weeks to allow the hMSCs to infiltrate and repopulate the valve. Within the culture vessel, the valve is then attached to a pump to allow the actuation of the valve leaflets and simulate the pumping motion present in the body. The valve is maintained in the pumping mode for 1-2 weeks to allow cellular remodeling associated with the stresses of the pumping action. Once sufficient cellular remodeling has occurred, the valve is implanted into the body of the patient.

Another embodiment of this aspect of the invention is to first repopulate the valve with hMSCs and to later incubate the valve tissue during the pumping stage with autologous smooth muscle cells isolated from a vascular graft which will line the lumen of the valve.

EXAMPLE 3

MSC Engraftment in Rat MI Model: Direct Injection vs. Systemic Delivery

Myocardial infarction was produced in Fisher rats as follows:

Fisher rats were given a cocktail of Ketamine/Xylazine/Acepromazine (8.5 mg/ 1.7 mg/0.3 mg I.P.) The depth of anesthesia was assessed using a toe-pinch and eye-blink reflexes. When a surgical plane of anesthesia was achieved, endotracheal intubation was performed and the animal placed on 1.0% Isoflorane. Positive-pressure breathing was provided throughout the procedure by means of the Engler ADS 1000 small animal ventilator. A left thoracotomy was performed and the pericardium opened. A 6-0 silk ligature snare was then placed around the left anterior descending (LAD) coronary artery at a location distal to the first diagonal branch. A brief (30 sec) LAD test occlusion is performed to insure that a modest region of ischemia is procued, involving a limited region of the anterior free wall and septum. lschemia is confirmed by characteristic ECG changes, ventricular dyskinesis and regional cyanosis. Myocardial infarction is then produced by occluding the LAD for a period of 45 minutes. At the completion of the 45 minute period, the snare is removed and reperfusion visually confirmed. The chest was then closed by approximating the ribs and all associated musculature. The Isoflurane is turned off, the animal removed from the ventilator and extubated.

Figure 2A:
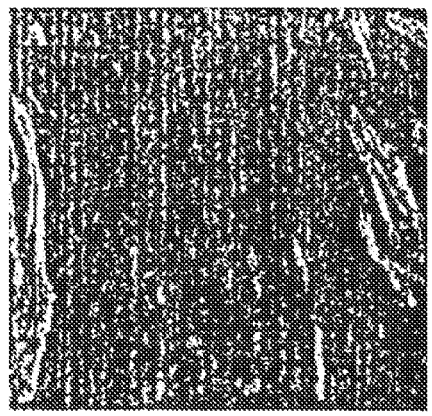
FIG. 2. Comparison of MSC engraftment when delivered to rats via direct cardiac injection (Panel A) or tail vein (Panel B). Confocal images were obtained in hearts harvested 4 weeks post-implantation.
Figure 2B:
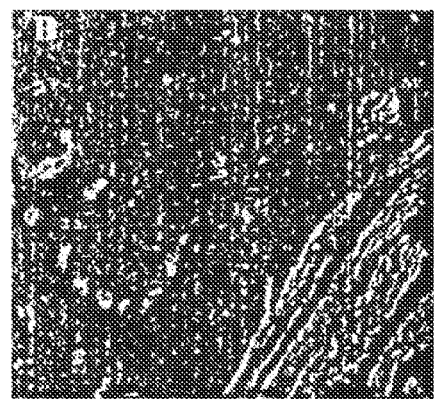

Panel A of FIG. 2 shows engraftment of MSCs in the heart following direct injection into the heart. In these experiments, $2-4 \times 10^6$ allogeneic rat MSCs were implanted into the area of necrosis by direct injection.

Panel B of FIG. 2 shows that tail vein injection results in cardiac engraftment.

These animals received MSCs via the tail vein. Injection of the allogeneic cell suspension occurred when the animals had stabilized, and a normal cardiac rhythm had been reestablished; usually within 15 minutes of reperfusion. At that time approximately $5 \times 10^6$ MSCs in a 0.5 milliliter suspension were injected slowly into the tail vein.

EXAMPLE 4

Swine are sedated with 1000 mg ketamine IM and brought into the lab. Intravenous access is established via an ear vein and the animals anesthetized with nembutal. Swine then are intubated, ventilated with 1.0-1.5% isoflurane, and prepped for surgery. ECG leads and rectal temperature probes are placed and the animal is draped to create a sterile field. A midline sternotomy is performed and the heart suspended in a pericardial cradle. A tygon catheter is placed in the apex of the left ventricle and sutured in place to measure ventricular pressure throughout the cardiac cycle. The left anterior descending (LAD) coronary artery is dissected free just distal to the first diagonal branch. A brief (30 sec) occlusion of the coronary artery is performed to identify the regions of ischemia (identified by the extent of cyanosis). Four piezoelectric crystals then are placed within regions destined for infarction.

At the completion of the surgical instrumentation a 15 minute stabilization period is allowed prior to obtaining baseline recordings. Following these recordings, the LAD there is occluded for a period of 60 minutes to produce myocardial infarction. Lidocaine (local anesthetic and antiarrhythmic) is administered at this time to reduce the incidence of ventricular fibrillation (2 mg/kg i.v. bolus plus 0.5 mg/min iv drip). Recordings of left ventricular pressure and regional contractile function are again obtained at 10 and 50 minutes of ischemia. Extensive cyanosis within the ischemic bed was noticed following 50 minutes of ischemia.

At the completion of the 60 minute period of ischemia, the snare is released and reperfusion established. Care is taken to ensure that perfusion is reestablished and that the isolated region of the LAD is not in spasm. At this time the leads (sono leads and LV catheter) are externalized, and the chest closed in layers. A chest tube is placed to reestablish a negative intrapleural pressure (tube is pulled 24 hrs later). The isoflurane is then turned off, and the animal is extubated and allowed to recover.

One set of infarcted swine was treated with allogeneic mesenchymal stem cells and another set (control) did not receive such treatment. The animals were examined using echocardiography. In the mesenchymal stem cell treatment, a 10 ml MSC suspension was drawn up into several 3 cc syringes using an 18 g needle. The needle was switched to a 30 g for delivery. Implantation was accomplished in the open chest setting. The needle was advanced to the mid-wall level, and 0.5 mls of cells were injected. This same procedure was performed approximately 20 times throughout the damaged area. Care was taken to provide cells to the entire apical anterior wall, as well as the septum. At the completion of the implantation procedure, the chest was closed and the animal allowed to recover.

Figure 3A:
FIG. 3 shows images indicative of anterior wall motion in infarcted swine hearts that received no treatment and those that were treated with allogeneic MSCs.
Figure 3B:
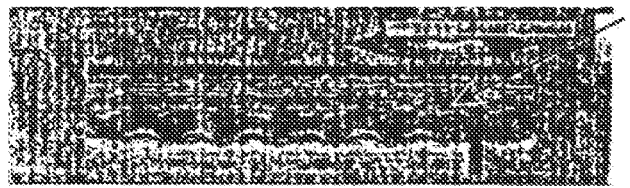

FIG. 3 contains "m-mode" images obtained in a control and an MSC treated animal. The image illustrates wall motion in a selected plane over time (moving left to right). The infarcted region of myocardium, consisting primarily of anterior LV free wall, is the structure highlighted by the arrows. That segment of myocardium is essentially akinetic in the control image, indicative of severe infarction/injury. While not quantifiable, there is improved anterior wall motion in the animal treated with allogeneic MSCs.

Echocardiography was used to measure the ejection fraction, a measure of global pump efficiency (a normal ejection fraction of 70% indicates that 70% of the LV volume is pumped with each beat of the heart; EF<40% is indicative of heart failure). Ejection fraction data is shown in the upper panels of FIG. 4. Control animals demonstrated no significant improvement in EF over the course of the study. In contrast, a statistically significant improvement in cardiac pump function was observed in MSC treated animals (right panel).

Figure 4:
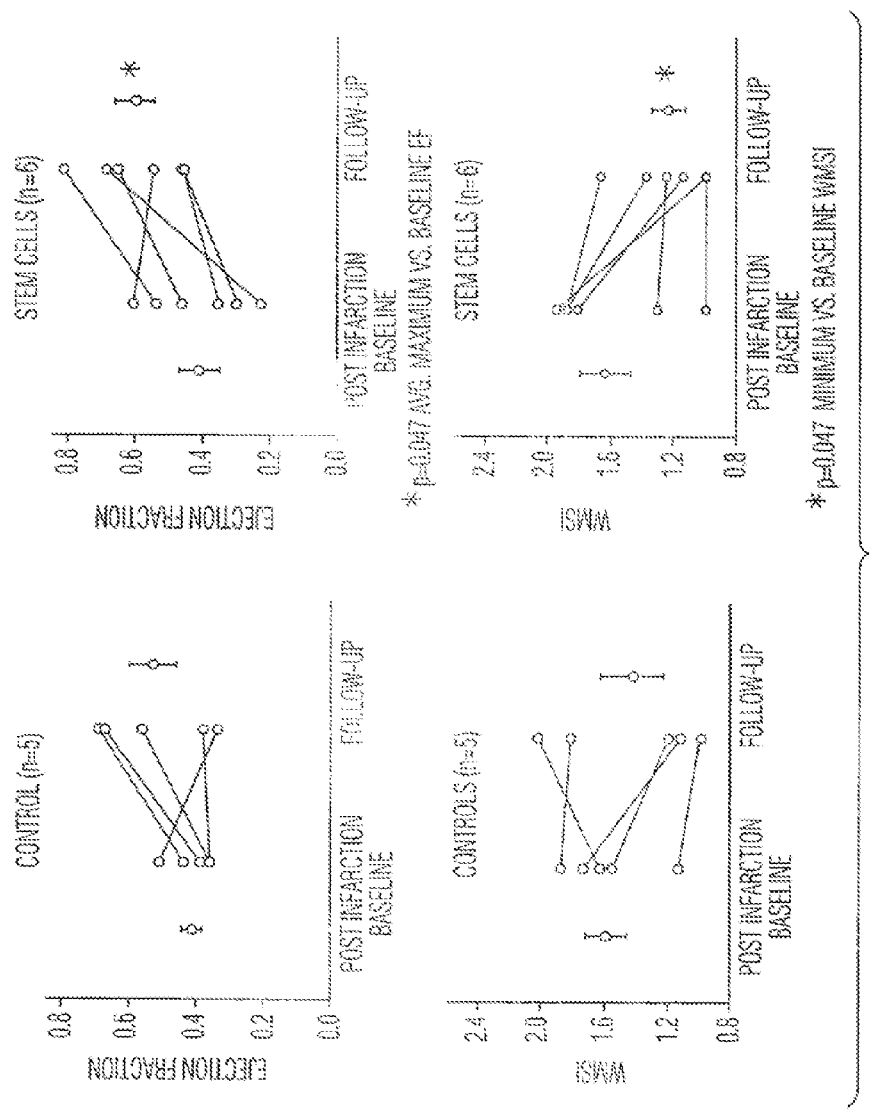
FIG. 4 shows graphs of ejection fraction (upper panels) measured in infarcted swine hearts that received no treatment and those that were treated with MSCs, and graphs of global wall motion (lower panels) in infarcted swine hearts that received no treatment, and those that were treated with MSCs.

A similar graph was used to represent wall motion score index (lower panels of FIG. 4). In this analysis, 17 segments of the left ventricle were examined for wall motion and scored on a scale of 1-5, with 1 representing "normal" wall motion. These segments, comprising all areas of the ventricle, can then be averaged to gather an index of global wall motion (i.e., global function). As with ejection fraction, no significant improvement in wall motion was observed in control animals over time. MSC treated animals showed consistent and significant improvements in wall motion scores over time (right panel).

Figure 5:
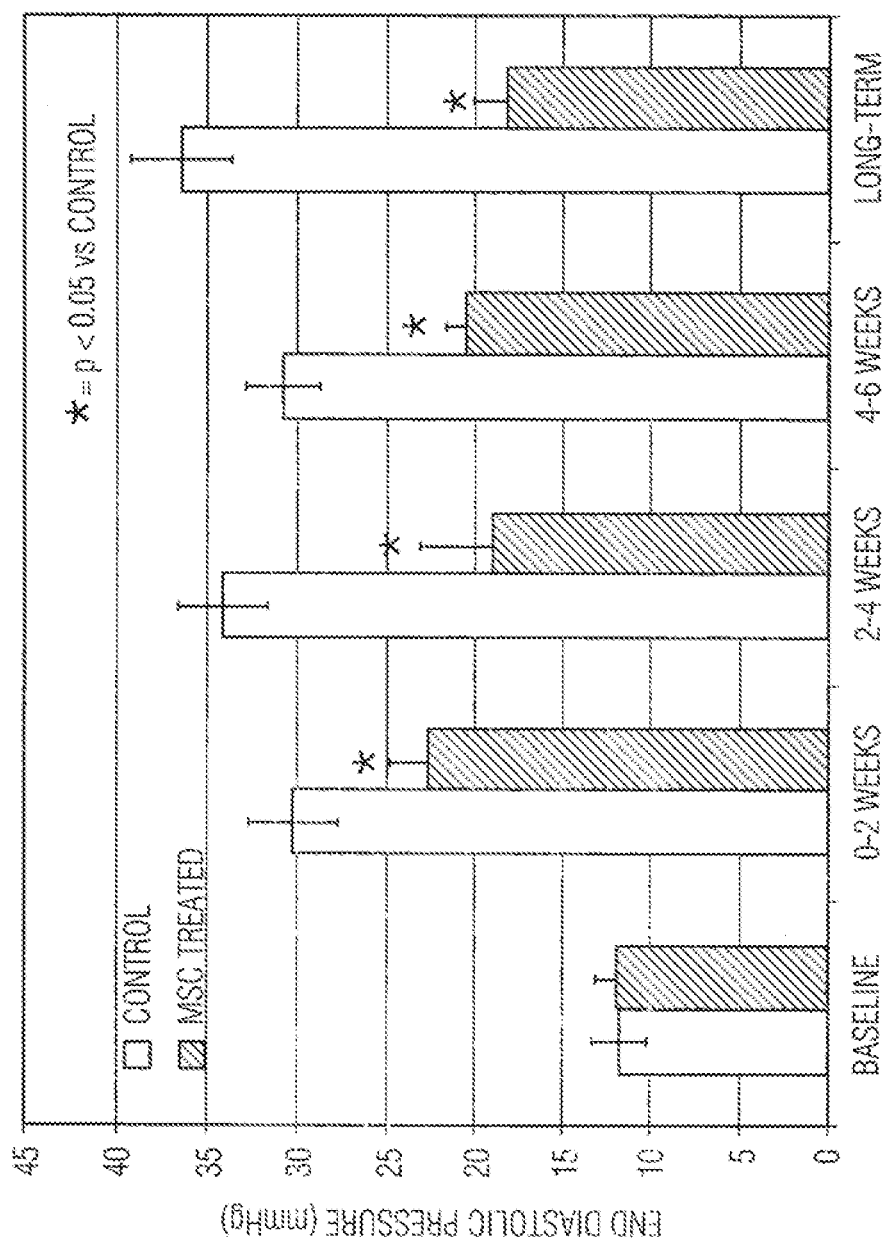
FIG. 5 is a graph of end diastolic pressure in infarcted swine hearts that received no treatment and those that were treated with MSCs.

Further evidence for improved cardiac function with MSC treatment is found when end diastolic pressure (EDP) is examined. When cardiac pump function is reduced following infarction, a pathologic increase in left ventricular EDP is observed. This increase in EDP is a clinically relevant finding that is often predictive of the progression to heart failure following infarction. As shown in FIG. 5, the EDP of control swine rose from approximately 12 to 35 mmHg in the 6 months following infarction. The rise in EDP in animals treated with MSCs was significantly attenuated at all time points examined post-infarction.

EXAMPLE 5

Pathologic ventricular remodeling following myocardial infarction is a major cause of heart failure. It was previously demonstrated that autologous mesenchymal stem cells (MSC) augment local systolic wall thickening and prevent pathologic wall thinning. Based on in vitro studies, it was hypothesized that MSCs may be immuno-privileged, and that implantation of allogeneic MSCs could prevent pathologic remodeling and improve cardiac performance in a swine model of myocardial infarction. Piezoelectric crystals and an LV catheter were implanted in domestic swine prior to a 60' LAD occlusion to produce infarction. Following reperfusion, treated animals (n=7) were injected with allogeneic Dil-labeled MSCs ($2 \times 10^8$ cells in 9 ml) throughout the region of infarction. Control (CON, n=6) received vehicle. Allogeneic donor MSCs were previously isolated from swine iliac crest bone marrow, expanded in culture, and cryopreserved until the time of implantation. Hemodynamic parameters and regional wall motion were evaluated in conscious animals bi-weekly using trans-thoracic echocardiography and sonomicrometry. Animals were sacrificed at various time points (6-24 weeks) and tissue harvested for histological examination. Implantation of allogeneic MSCs was not associated with ectopic tissue formation, significant inflammatory response or any adverse clinical event. Robust engraftment of allogeneic MSCs was observed in all treated animals. Furthermore, engrafted MSCs were found to express numerous muscle specific proteins, and exhibited morphological changes consistent with myogenesis. A marked improvement in both ejection fraction ($55 \pm 9.4\%$ vs $32.5 \pm 12.5\%$ in CON) and global wall motion score ($1.45 \pm 0.15$ vs $2.1 \pm 0.2$ in CON) was observed in treated animals at 10 weeks post-MSC implantation. Systolic wall thickening and diastolic wall thickness were also augmented in MSC treated animals. Because no significant difference in infarct size or cardiac loading was noted between groups, improvements in cardiac function are likely attributable to MSC implantation. In conclusion, this example suggests that implantation of allogeneic MSCs at reperfusion may be an effective therapeutic option to prevent or reverse the progression to heart failure following infarction.

The above examples illustrate that mesenchymal stem cells augment ventricular function, as shown, for example by improved cardiac ejection fraction and global wall motion.

EXAMPLE 6

A pig was subjected to a 60 minute LAD occlusion to produce infarction as described in Example 5. Three days after the infarction, $200 \times 10^6$ diaminopropidium iodide (DAPI)-labeled allogeneic mesenchymal stem cells were administered to the left ventricular wall by endocardial catheter as 20 separate injections of $10 \times 10^6$ cells each in 0.5 ml physiological saline. DAPI is a nuclear stain which emits a strong blue fluorescence and aids in the identification of implanted cells.

Eight weeks after administration of the mesenchymal stem cells, the pig was sacrificed, and the heart was harvested for histological examination. Sections were subjected to hematoxylin and eosin staining, or to fluorescence imaging after being contacted with an FITC-labeled monoclonal antibody against smooth muscle actin.

Figure 6A:
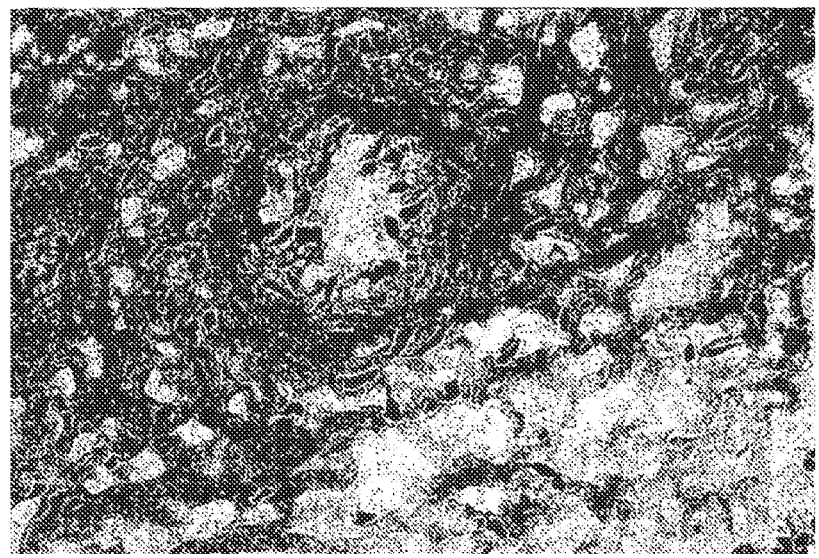
FIGS. 6A and 6B show sections of an infarcted region of a pig heart at 8 weeks after being treated with DAPI-labeled mesenchymal stem cells. Both figures show the presence of blood vessels in the infarcted region.

The hematoxylin and eosin image (FIG. 6A) clearly illustrates the presence of blood vessels within a generalized region of myocardial necrosis.

Figure 6B:
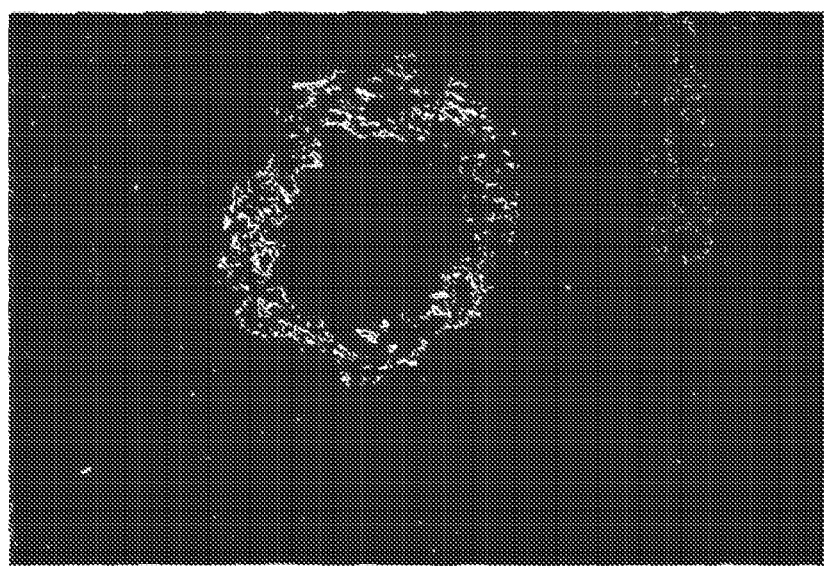

As shown in FIG. 6B, DAPI-labeled cells can be seen throughout the section; however, a localization of implanted MSC's can be identified readily. These MSC's surround, and are associated with, the blood vessels.

As shown in FIG. 6B, the lighter, or green, fluorescence indicates the presence of the FITC-labeled monoclonal antibody against smooth muscle actin, thus indicating the presence of a blood vessel. Also present in FIG. 6B are DAPI-labeled (blue) MSC's localized within such vessel, and which are associated intimately with the smooth muscle layer of the vessel. Thus, the MSCs are involved in the repair or regeneration of blood vessels of the heart.

EXAMPLE 7

A pig was subjected to a 60 minute LAD occlusion to produce infarction as described in Example 5. Three days after the infarction; the pig was given $200 \times 10^6$ diaminopropidium iodide (DAPI)-labeled allogeneic mesenchymal stem cells as 20 separate injections of $10 \times 10^6$ cells in 0.5 ml physiological saline into the left ventricular wall by endocardial catheter as described in Example 6.

Twelve weeks after administration of the mesenchymal stem cells, the pig was sacrificed, and the heart was harvested for histological examination. Sections were subjected to hematoxylin and eosin staining, or to fluorescence imaging after being contacted with an FITC-labeled monoclonal antibody against Factor VIII (Von Willebrand Factor) or an FITC-labeled monoclonal antibody against vascular endothelial growth factor (VEGF).

Figure 7A:
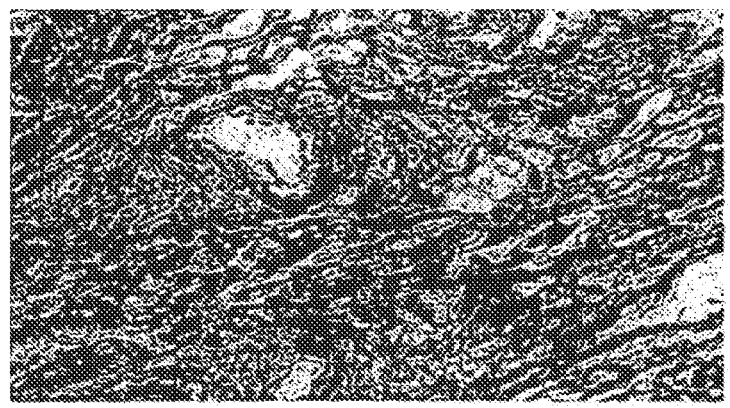
FIGS. 7A through 7E show sections of an infarcted pig heart at 12 weeks after being treated with DAPI-labeled mesenchymal stem cells. The figures show the presence of blood vessels in the infarcted region.
Figure 7B:
Figure 7C:
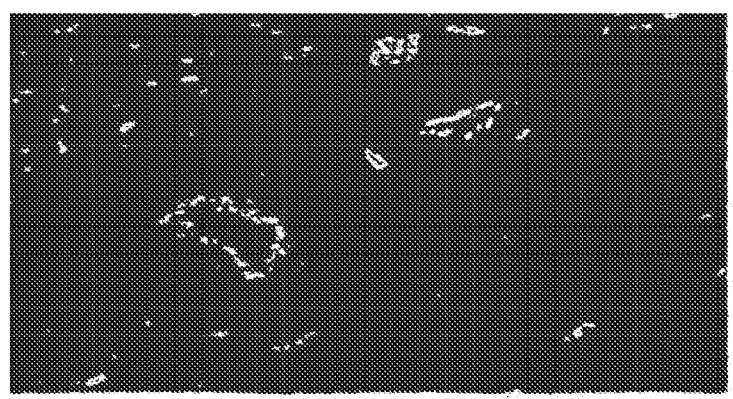
Figure 7D:
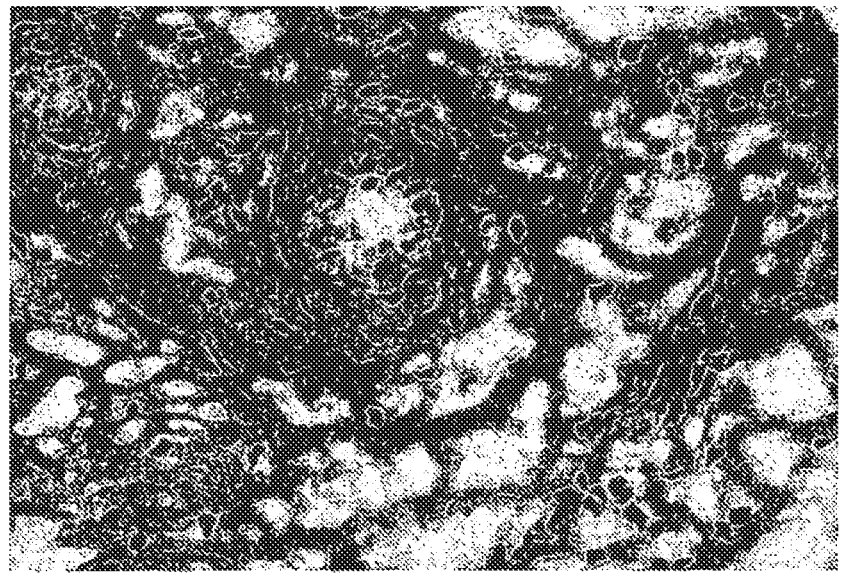

As shown in the hematoxylin and eosin images of FIGS. 7A and 7D, the presence of blood vessels within a region of generalized myocardial necrosis is illustrated.

Figure 7E:
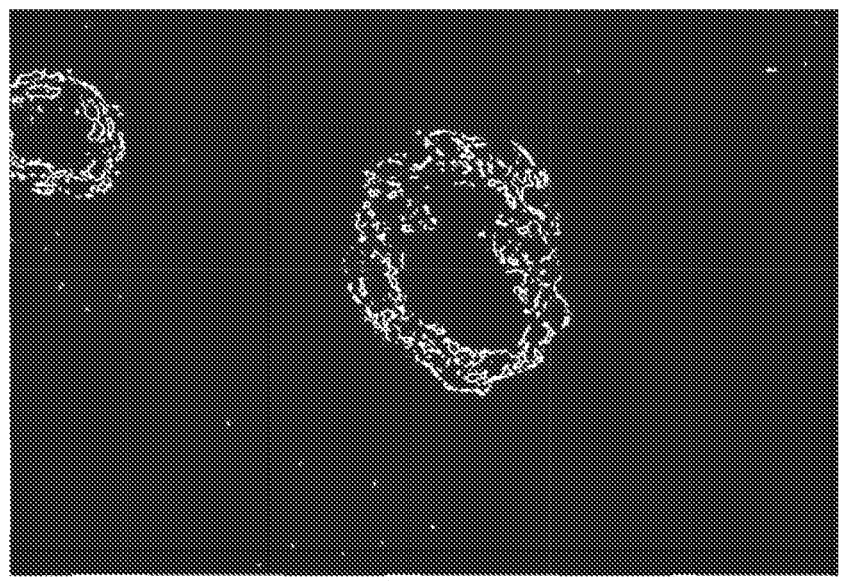

In the fluorescent images of FIGS. 7B, 7C and 7E, DAPI labeled cells can be seen throughout the sections; however, localizations of MSCs can be identified which surround and are associated intimately with the smooth muscle layer of the blood vessels. Light, or green, fluorescence indicates the presence of FITC-labeled monoclonal antibody against Factor VIII (FIG. 7C) or against VEGF (FIG. 7E).

Thus it has been shown that the implanted MSCs express Factor VIII and VEGF, which are indicative of angiogenesis. These proteins are not expressed by cultured MSCs, but are expressed only after several weeks in the cardiac environment.

The disclosure of all patents and publications (including published patent applications) are hereby incorporated by reference to the same effect as if each patent and publication were individually and specifically incorporated by reference.

It is to be understood, however, that the scope of the present invention is not to be limited to the specific embodiments described above. The invention may be practiced other than as particularly described and still be within the scope of the accompanying claims.

The invention claimed is:

1. A method for treating a patient with myocardial infarction comprising:
   administering to the patient human allogeneic mesenchymal stem cells in an amount effective to improve cardiac function following myocardial infarction.

2. The method of claim 1, wherein the mesenchymal stem cells are administered intravenously.

3. The method of claim 1, wherein the mesenchymal stem cells are administered in a pharmaceutically acceptable liquid carrier.

4. The method of claim 3, wherein the pharmaceutically acceptable carrier comprises an isotonic liquid.

5. The method of claim 4, wherein the isotonic liquid comprises phosphate buffer saline, physiological saline, culture medium, or 5% dextrose in water.

6. The method of claim 4, wherein the pharmaceutically acceptable carrier comprises phosphate buffer saline.

7. The method of claim 1, wherein the mesenchymal stem cells are administered in a suspension containing about $10 \times 10^6$ to about $40 \times 10^6$ mesenchymal stem cells per ml.

8. The method of claim 7, wherein the suspension is administered in an amount of about 20 µl to about 150 ml.

9. The method of claim 7, wherein the suspension is administered in an amount of at least about 20 µl.

10. The method of claim 7, wherein the suspension is administered in an amount of at least about 500 µl.

* * * * *